United States Patent [19]

Williams

[11] Patent Number: 5,284,974
[45] Date of Patent: Feb. 8, 1994

[54] PROCESS FOR THE PREPARATION OF THIOACETAMIDE

[75] Inventor: Eric L. Williams, St. Ann, Mo.

[73] Assignee: Monsanto Company, St. Louis, Mo.

[21] Appl. No.: 927,997

[22] Filed: Aug. 11, 1992

[51] Int. Cl.⁵ .......................................... C07C 327/00
[52] U.S. Cl. ..................................................... 564/74
[58] Field of Search .................. 564/74; 502/162, 164

[56] References Cited

U.S. PATENT DOCUMENTS

| 2,421,031 | 5/1947 | Mahan | 266/551 |
| 3,700,664 | 10/1972 | Girgis | 260/247.1 |
| 3,852,287 | 12/1974 | Girgis | 260/247.1 |

FOREIGN PATENT DOCUMENTS

| 946392 | 4/1974 | Canada. |
| 0272909 | 6/1988 | European Pat. Off.. |
| 0277824 | 8/1988 | European Pat. Off.. |
| 9003368 | 4/1990 | World Int. Prop. O.. |

OTHER PUBLICATIONS

Jaworski and Terpinski, "Simple Synthesis of Ethanethioamide", *Polish J. of Chem.* 52, 2067 (1978).

*Primary Examiner*—Richard L. Raymond
*Assistant Examiner*—P. O'Sullivan
*Attorney, Agent, or Firm*—Grace L. Bonner; Stanley M. Tarter; Joan Thierstein

[57] ABSTRACT

An improved process for the reaction of acetonitrile and hydrogen sulfide to produce thioacetamide, wherein a polymer-supported amine catalyst is used. Examples of the polymer-supported amine catalyst are polymeric dimethylaminopyridine resins, poly(4-vinylpyridine) cross-linked with divinylbenzene, and cross-linked polymer-supported 4-(N-benzyl-N-methylamino)pyridine.

6 Claims, No Drawings

PROCESS FOR THE PREPARATION OF THIOACETAMIDE

FIELD OF THE INVENTION

The present invention provides an improved process for the production of thioacetamide from hydrogen sulfide and acetonitrile.

BACKGROUND OF THE INVENTION

Thioacetamide is a commercially available chemical having many industrial uses and is a versatile reagent for further chemical synthesis. The reaction of hydrogen sulfide and acetonitrile to produce thioacetamide is well known. U.S. Pat. No. 2,421,031 discloses the use of a catalyst, 8-14 mesh $SiO_2Al_2O_3$ gel, at a temperature of about 500° F. to obtain yields of 85% based on hydrogen sulfide. The reaction is also catalyzed by various bases. Jaworski, et al., disclosed the use of triethylamine in a 220-hour reaction carried out in benzene or toluene (*Polish J. Chem.*, 52 (10): 2067-8, 1978). Girgis disclosed the use of amine catalysts, including secondary amines (Canadian Pat. No. 946,392, 1974; U.S. Pat. No. 3,852,287, 1974; U.S. Pat. No. 3,700,664, 1972). More recently, alkyl metal sulfides and hydrosulfides have been disclosed as catalysts for the reaction of aminonitriles with hydrogen sulfide for the production of aminothioacetamides (Moder et al., EP 0 272 909). Moder et al. prefer these catalysts because the amine base catalysts previously used are difficult to remove after completion of the reaction.

It is an object of the present invention to provide a high-yielding, cost-effective process to prepare thioacetamide with minimal post-reaction processing and reusable catalysts.

SUMMARY OF THE INVENTION

The present invention provides a process for preparing thioacetamide from hydrogen sulfide and acetonitrile in the presence of a polymer-supported amine catalyst. The reaction is run under pressure due to the use of hydrogen sulfide gas. The reaction temperature is not crucial, but for commercially reasonable reaction times, it is preferred that the temperature be maintained between about 100° and 200° C., although some decomposition of the desired product may occur at the higher temperatures. Thus, it is preferred that the temperature not exceed 150° C., and more preferably it is maintained between about 120° and 130° C.

DETAILED DESCRIPTION OF THE INVENTION

The reactants used in the present invention are commercially available. They may be used in essentially equimolar amounts or acetonitrile may be used in molar excess to hydrogen sulfide. A molar excess of acetonitrile will result in a product which is a solution of thioacetamide in acetonitrile, which may facilitate handling the thioacetamide and may also be the desired form of thioacetamide for subsequent reaction(s) such as that shown below.

The reaction may be conducted in batches or as a continuous reaction, as in a tube reactor. The relative amount of catalyst needed to efficiently carry out the present process will depend on the reactor size and configuration, as well as the efficiency of mixing and heat exchange. The polymer-supported amine catalysts useful in the present invention have a range of effectiveness. The usual process development experimentation known to those of skill in the art will be needed to determine the optimum conditions; however, the examples below provide guidance as to effective combinations.

The polymer-supported amine catalyst may be any polymer which has pendant amino functionalities. The amine may be an alkyl or aryl amine or a heterocycle, such as pyridine. The polymer-supported amine may also be cross-linked with a second polymer type. For ease in removal and recycling it is preferred that the polymer-supported amine catalyst be insoluble in acetonitrile. Examples are heterogeneous gels or macroreticular resins such as a poly(4-vinylpyridine) cross-linked with a divinylbenzene polymer; a 25% cross-linkage has been found to be effective in the present invention. Further example are polymers having pendant 4-dimethylaminopyridine (DMAP) groups or 4-(N-benzyl-N-methylamino)pyridine (BMAP). The backbone polymer may be, for example, a polystyrene. A polymer having DMAP groups is a preferred embodiment in the present invention.

Polymer-supported amine catalysts are available in many forms from many sources. One such source is Reilly Tar & Chemical Corporation (Indianapolis). References for how to make such polymer-supported amine catalysts are discussed in PCT Application WO 90/03368 (April 1990), herein incorporated by reference. European Patent Application 0 277 824 also discloses such polymer-supported amine catalysts and their use in acetic acid production.

The polymer-supported amine catalyst has many advantages. First, it is not soluble in acetonitrile and thus may be recovered from the reaction by filtration. Alternatively, the reactants are exposed to a container of the catalyst which is porous to the reactants but not the catalyst, such a basket suspended in a reaction vessel or attached to the walls or baffles within a reaction tube.

Second, the catalyst requires no regeneration step before it can be used again. Contamination with the reactants or thioacetamide does not reduce its efficacy in succeeding reactions. Third, the reaction may be carried out at moderate temperatures which permit essentially 100% yield with little or no decomposition.

EXAMPLE 1

A mixture of 500 mL of acetonitrile and 10 grams of Reilex ® 425 or Reilly Poly-DMAP resin (Reilly Tar & Chemicals) is introduced into a one-liter autoclave. The solution is stirred and heated to 110°-130° C. Hydrogen sulfide gas (34 g, 1.0 mol) is introduced. The pressure decreases from about 145 psi to 40 psi as the hydrogen sulfide reacts with the acetonitrile. The reaction takes from 2 to 18 hours, after which the mixture is discharged from the reactor and filtered. The filtrate is an approximately 2M solution of thioacetamide in acetonitrile. The yields for variations of this reaction are reported below. The yield is reported as a percent of the consumption of hydrogen sulfide in the reaction.

| Catalyst | Time (h) | Temp (°C.) | Yield |
| --- | --- | --- | --- |
| Reilex ® 425 | 18 | 120 | 100 |
| Reilex ® 425 | 3 | 130 | 100 |
| Reilly Poly-DMAP | 2.25 | 120 | 100 |

Each of these catalysts have been used in three consecutive reactions with no loss of effectiveness in the present invention. It is expected that polymer-supported amine catalysts may be used many times in the present process without substantial loss of catalytic effectiveness.

One use of the solution of thioacetamide in acetonitrile is in the preparation of thiazole or derivatives thereof. The following example demonstrates such a reaction of thioacetamide and ethyl 4,4,4-trifluoro-2-chloroacetoacetate to produce ethyl 2-methyl-4-(trifluoromethyl)thiazole-5-carboxylate, which may in turn be used to produce fungicidal thiazolecarboxanilides. The process used in the following example is more fully described and disclosed in copending U.S. Ser. No. 07/927,981, filed, Aug. 11, 1992; herein incorporated by reference.

EXAMPLE 2

Preparation of a Thiazole Derivative

A solution of thioacetamide in acetonitrile (6.66 mol), prepared as in Example 1, is placed in a flask. Ethyl 2-chloro-4,4,4-trifluoroacetoacetate (5.06 mol) is added and an exotherm is observed. Triethylamine (13.64 mol) is added and the mixture is heated to reflux (approx. 76° C.) for one hour. The resulting solution is cooled. Ethyl 2-methyl-4-(trifluoromethyl)-thiazole-5-carboxylate may be isolated by standard means.

What is claimed is:

1. A method for the production of thioacetamide comprising contacting acetonitrile with hydrogen sulfide in the presence of a catalytically effective amount of polymer-supported amine catalyst.

2. The method of claim 1 wherein the reaction is carried out at a temperature between 100° and 150° C.

3. The method of claim 2 wherein the reaction is carried out at a temperature between 120° and 130° C.

4. The method of claim 1 wherein acetonitrile is in molar excess to hydrogen sulfide.

5. The method of claim 1 wherein said polymer-supported amine catalyst comprises 4-dimethylaminopyridine groups pendant to a polymer backbone.

6. The method of claim 1 wherein said polymer-supported amine catalyst is a macroreticular resin bead.

* * * * *